(12) United States Patent
Goldau

(10) Patent No.: US 6,217,539 B1
(45) Date of Patent: *Apr. 17, 2001

(54) METHOD OF IN-VIVO DETERMINATION OF HEMODIALYSIS PARAMETERS AND A DEVICE FOR CARRYING OUT THE METHOD

(75) Inventor: Rainer Goldau, Rimpur (DE)

(73) Assignee: Fresenius Medical Care Deutschland GmbH, Bad Homburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/979,401

(22) Filed: Nov. 26, 1997

(30) Foreign Application Priority Data

Nov. 30, 1996 (DE) ............................................. 196 49 776

(51) Int. Cl.$^7$ .................................................. A61M 37/00
(52) U.S. Cl. ....................... 604/4.01; 604/5.04; 210/739; 600/366; 600/454
(58) Field of Search ............................ 604/4, 28–9, 4.01, 604/5.01, 6.1, 6.09; 128/898; 600/363, 366, 454; 210/645–47, 650, 739

(56) References Cited

U.S. PATENT DOCUMENTS

| | | | |
|---|---|---|---|
| 4,366,061 | * 12/1982 | Papanek et al. | 210/647 |
| 4,399,036 | * 8/1983 | Babb et al. | 210/638 |
| 4,722,798 | * 2/1988 | Goss | 210/646 |
| 5,092,836 | 3/1992 | Polaschegg . | |
| 5,100,554 | * 3/1992 | Polaschegg | 210/647 |
| 5,110,477 | 5/1992 | Howard et al. . | |

(List continued on next page.)

FOREIGN PATENT DOCUMENTS

| | | |
|---|---|---|
| WO 97/10013 | 3/1997 | (DE) . |
| 197 34 9927 | 10/1998 | (DE) . |
| 0 097 366 | 9/1988 | (EP) . |
| 291 421 | 11/1988 | (EP) . |
| 330 892 | 9/1989 | (EP) . |
| 39 38 662 | 7/1991 | (EP) . |
| 547 025 | 6/1993 | (EP) . |

*Primary Examiner*—Angela D. Sykes
*Assistant Examiner*—Patricia Bianco
(74) *Attorney, Agent, or Firm*—Kenyon & Kenyon (57) ABSTRACT

To be able to optimize the hemodialysis treatment process, in-vivo determination of important parameters, such as the exchange efficiency of the dialyzer, represented by the dialysance or clearance, is desirable. Mathematical quantification of the blood purification processes on the basis of measurement technology is especially important. Important measured quantities and operands for the determination of the desired parameter are usually the dialysate flow and the blood flow (Qd, Qb), the inlet and outlet concentrations (cdi, cdo) of the dialysis fluid and the electrolyte transfer rate derived from it as well as the formulation of the mass balance in the dialyzer.

This invention provides that at least one of the two flow rates (Qb, Qd) is set at a minimum of two different values in the measurement interval, and corresponding measured quantities are derived, from which the parameter to be determined is obtained together with the above-mentioned conventional measured quantities and operands as well as on the basis of equations between the dialyzer characteristics that describe the mass exchange and a conditional equation. At a known effective blood flow (Qb), this may be, for example, the blood concentration at the inlet (cbi), from which the dialysance can then be determined. When the cbi value is known, the effective blood flow and thus the hematocrit can be determined.

13 Claims, 1 Drawing Sheet

U.S. PATENT DOCUMENTS

| | | | | |
|---|---|---|---|---|
| 5,230,341 | * | 7/1993 | Polaschegg | 128/668 |
| 5,261,874 | * | 11/1993 | Castle | 604/4 |
| 5,442,969 | * | 8/1995 | Troutner et al. | 73/863.71 |
| 5,507,723 | * | 4/1996 | Keshaviah | 604/5 |
| 5,567,320 | * | 10/1996 | Goux et al. | 210/739 |
| 5,685,989 | * | 11/1997 | Krivitski et al. | 210/646 |
| 5,744,031 | * | 4/1998 | Bene | 210/321.71 |
| 5,849,179 | * | 12/1998 | Emerson et al. | 210/87 |
| 5,866,015 | * | 2/1999 | Krämer | 210/739 |

* cited by examiner

METHOD OF IN-VIVO DETERMINATION OF HEMODIALYSIS PARAMETERS AND A DEVICE FOR CARRYING OUT THE METHOD

FIELD OF THE INVENTION

The invention relates to a method of in-vivo determination of hemodialysis parameters, and to a device for carrying out the method.

BACKGROUND OF THE INVENTION

Hemodialysis has been used successfully for many years for treatment of patients with renal failure and has proven successful throughout the world.

Human kidneys have several functions, e.g., eliminating water, removing metabolic waste products (urea, creatinine) and helping to adjust the concentrations of various substances such as blood electrolytes (sodium, bicarbonate, etc.) at certain levels.

Hemodialysis is a treatment method for compensating for renal dysfunction by removing metabolic waste products and helping to adjust the blood electrolyte concentrations.

This treatment method is carried out with a dialyzer, which is essentially an exchanger with two chambers separated from each other by a semi-permeable membrane, a blood chamber for connection to an extracorporeal blood circulation and a chamber for a dialysis fluid which is connected to a container for dialysis fluid in a dialysate circuit. A classical dialysate fluid contains the main blood electrolytes in a concentration close to the concentrations in the blood of a healthy person.

During a treatment, the patient's blood and the dialysis fluid are passed by both sides of the membrane, usually in countercurrent flow, at a predetermined flow rate. The metabolic elimination products diffuse through the membrane from the blood chamber to the chamber for dialysis fluid, while the electrolytes present in the blood and in the dialysis fluid at the same time diffuse from the chamber with a higher concentration to the chamber with a lower concentration. The metabolism can also be influenced by applying a transmembrane pressure (ultrafiltration).

To be able to optimize the treatment method, hemodialysis parameters must be determined in vivo, i.e., while the procedure is being carried out. One such parameter in particular is the value for the exchange efficiency of the iS dialyzer, represented by the "clearance" or "dialysance D." The following definitions are conventional:

According to DIN 58,352, part 1, the clearance for a certain substance K denotes the virtual (calculated) blood volume from which this substance is removed completely by the dialyzer per minute.

Dialysance is another term for determining the efficiency of a dialyzer, which also takes into account the concentration of the substance in the dialysis fluid which is involved in the mass exchange in the dialyzer.

In addition to these dialyzer performance characteristics, other parameters are also important, in particular the values of the aqueous portion of the blood (the effective blood flow), the hematocrit and the blood concentration at the inlet.

It is relatively complex to quantify mathematically the blood purification methods on the basis of measurement technology and, in conjunction with this, to determine the above-mentioned parameters of dialysis. Reference is made in this regard to the book by H. E. Franz, Blutreinigungsverfahren [Blood Purification Methods], published by Georg Thieme Verlag, Stuttgart, New York, 1990, specifically pages 479–492.

Accordingly, the following is obtained in particular for determining the dialysance or the clearance for a given electrolyte, e.g., sodium as the substance, if there is no ultrafiltration. The dialysance D is equal to the ratio of the mass transport for this electrolyte on the blood side Qb×(cbi−cbo) and the difference in concentration of this electrolyte between the blood and the dialysis fluid at the inlet of the dialyzer (cbi−cdi).

$$D = Qb \frac{(cbi - cbo)}{cbi - cdi} \qquad (1)$$

For reasons of mass balance (the quantity of substance removed from the blood is equal to the quantity of substance carried away in the dialysate in the same period of time), the following holds:

$$QB \cdot (cbi - cbo) = -Qd \cdot (cdi - cdo) \qquad (2)$$

It follows from (1) and (2) for the dialysance on the dialysate side that:

$$D = -Qd \frac{(cdi - cdo)}{cbi - cdi} \qquad (3)$$

where in (1) to (3):
Qb=effective blood flow
Qd=dialysis fluid flow
cb=concentration of the substance in the solution volume of the blood
cd=concentration of the substance in the dialysis fluid
i=inlet of the dialyzer
o=outlet of the dialyzer The effective blood flow is the flow of the blood component in the whole blood flow in which the substances to be removed are dissolved, i.e., it is based on the complete (aqueous) solution volume for this substance. Depending on the substance, this may be the plasma water flow or the blood water flow, i.e., the total amount of water in the whole blood.

For the case of a specific metabolic elimination product (such as urea), cdi=0, and then we speak of the clearance K for this metabolic product instead of the dialysance.

$$K = Qb \frac{(cbi - cbo)}{cbi} = Qd \frac{cdo}{cbi}$$

All the known methods of in-vivo determination of hemodialysis parameters begin with these considerations, most of which have in common the attempt to avoid a direct measurement procedure on the blood side because this could represent a not insignificant source of risks. Therefore, there has been an effort to derive the quantities of measured values that are to be determined merely from measurements on the dialysate side, even with regard to the quantities on the blood side. A customary basic method is to measure the concentration of the substance in the dialysis fluid upstream and downstream of the dialyzer and then calculate from this the mass transport on the dialysate side Qd×(cdi−cdo), and derive from these values by means of the above equations other quantities, in particular the value for the blood concentration at the inlet cbi, which enters into the equations as a mathematical unknown. The two values cdi and cdo need not necessarily be measured. The inlet value cdi can also be adjusted in a defined manner in the fresh dialysis fluid.

If the value cbi of an electrolyte is to be determined in particular, cdi and cdo can be determined by conductivity measurements. In the case of NaCl, a nonspecific measurement is sufficient, because NaCl is responsible for most of the conductivity of the fluids involved. This basic method is known from European Patent EP 97,366.

Starting from the preceding basic method, the individual known methods differ in the methods of measurement and analysis. They will be explained in greater detail below.

European Patent EP 291,421 B1 discloses a method of determining the blood concentration at the inlet, where the dialysate inlet concentration is varied according to a ramp function to determine the point at which there is no further transfer of electrolyte across the membrane. Therefore, the known method works according to the principle of varying the inlet conductivity of the dialysis fluid to the extent that it no longer differs from the outlet conductivity. Then it must have assumed the blood input conductivity (cbi=cdi). Other parameters of hemodialysis can then be derived on the basis of equations (1) through (3). A disadvantage of this method is the relatively long measurement time due to the period of time until reaching the stable equilibrium state in adjusting the dialysis fluid at the new input concentration value, which is not immediately effective at each point in the dialyzer. Due to the system, a certain amount of time is required until a jump in conductivity at the dialysate inlet leads to stable conditions at the dialysate outlet. The period of time required to reach the stable equilibrium state is determined essentially by the extent of the change in conductivity per unit of time. Within this long period of time, however, parameters of dialysis can change and can thus falsify the value to be determined. It should be noted in particular that the known method mentioned above (like all other methods) can change the blood concentration at the inlet cbi through the induced electrolyte transfer. In the known case, this systematic error is especially great due to the type of change in concentration on the dialysate side. The known method thus does not lead to accurate measured values for the hemodialysis parameters to be determined in vivo. In addition, relatively complicated additional equipment is required to vary the dialysate inlet concentration.

Another method of in-vivo determination of hemodialysis parameters has also become known from German Patent DE 3,938,662 C2 (=European Patent EP 428,927 A1). In this method, the dialysate electrolyte transfer is measured at two different dialysate inlet concentrations. Then the dialysance can be determined on the basis of equation (3) for these two cases and the assumption that cbi is constant; this is done by determining the difference between the differences between the dialysis fluid ion concentrations at the inlet side and the outlet side of the dialyzer at the time of the first and second measurements, then dividing this value by the difference between the dialysis fluid ion concentration at the inlet side at the time of the first measurement and the second measurement and then multiplying the quotient by the dialysis fluid flow.

In this method it must also be assumed that the blood concentration at the inlet cbi in the two measurements remains unchanged, because otherwise the corresponding equation system could not be solved for the blood inlet concentration cbi with a determination of the dialysance.

However, an increase in the dialysate inlet concentration cdi also increases the blood concentration at the inlet. In addition, a constant dialysance with a change in inlet and outlet conductivity is assumed with the known method. However, no verifiable information is known about the limits of validity of this assumption. Like all methods with a change in dialysate inlet concentration, this method also requires an additional device for varying the dialysate inlet concentration.

In a refinement of the known method, it is also provided that the dependance of the parameters determined, e.g., the dialysance, on the dialysis fluid flow is additionally determined. To do so, the dialysis fluid flow is set at different values, and the dialysance for each of the flow values is measured at two different dialysate concentrations on the basis of the measurement of the dialysate-electrolyte transfer.

Another relevant method which has as its goal mainly the determination of the blood concentration at the inlet cbi is known from European Patent EP 330,892 A1 and the patent of separation from it, European Patent EP 547,025. In this connection, a method is also given for determining the relative dialysance D/Qd, where the difference in the dialysis fluid ion concentration at the inlet and outlet sides of the dialyzer, i.e., the electrolyte transfer rate, is determined. To determine D/Qd, the conductivity, i.e., the ion concentration, in the dialysis fluid is varied incrementally, where the relative dialysance for each conductivity value is determined by the respective measurement of the electrolyte transfer.

Therefore, this known method likewise works with different concentration settings in the dialysate circuit with the disadvantages mentioned above (long measurement times, complicated equipment, etc.), especially since in the known case "the equation only comes out even" when the equilibrium situation cbi=cdi to the prior determination of cbi is awaited when there is a change in concentration in addition to waiting for a stable state to be established on the dialysate side.

U.S. Pat. No. 5,567,320 describes a method of determining hemodialysis parameters involved in mass exchange, such as the blood inlet concentration or dialysance, where the dialysis fluid in the measurement interval is set at three different concentrations of the substance in question at a constant blood flow or dialysis fluid flow.

Therefore, this known method also works with different successive concentration settings in the dialysate circuit with the above-mentioned consequence of the expensive equipment, the relatively long measuring time and the reactive effect on the blood concentration at the inlet.

U.S. Pat. No. 5,110,477 discloses a method of determining the clearance of a dialyzer wherein calibration solutions are passed through the dialyzer on both the dialysate side and the blood side. The dialysance or clearance can be deduced on the basis of comparisons with setpoints. This method has the disadvantage that it is complicated and cannot be carried out "in vivo" but can only be performed "in vitro," i.e., outside the ongoing dialysis treatment.

World Patent WO 95/32010 discloses a method of optimizing the settings in the dialysis treatment, where a parameter, in particular the blood flow, is varied in such a way as to achieve an optimum removal of harmful substances (=maximum dialysance). The concentration of a metabolite (urea) is measured directly at the dialysate outlet, and the blood flow is varied until the concentration reaches a maximum. However, this method is very time consuming and is limited to optimizing the elimination.

OBJECT AND SUMMARY OF THE INVENTION

The object of this invention is to make the in-vivo determination of hemodialysis parameters faster and more accurately than in the state of the art.

On the basis of the known methods cited in the introduction, this object is achieved through means of a dialyzer with a semipermeable exchange membrane which separates a blood chamber from a dialysate chamber. The blood to be purified flows at a predetermined flow rate through an extracorporeal circulation system and through the dialyzer. Likewise the dialysis fluid flows at a predetermined rate through the dialyzer. The invention further entails the use of at least one predetermined substance concentration and/or the substance concentration in the d dialysis fluid is determined upstream and downstream of the dialyzer at measured intervals. According to the invention, the flow rate of either the blood or the dialysis fluid is set at a minimum of two different values and the corresponding measured flow quantities are obtained. The parameter to be determined is derived from the measured concentrations and flow quantities on the basis of relationships between the dialyzer characteristics describing the mass exchange.

On the basis of the device cited in the introduction, this object is achieved by a device comprising a dialyzer having a semipermeable membrane which separates a blood chamber from a dialysate chamber. The blood chamber being connected to an extracorporeal circulation having a blood pump with a device for setting the pump speed and thus the whole blood flow. The dialysate chamber being connected to a dialysate circuit having a dialysate pump with a respective device for setting the pump speed and thus the dialysis fluid flow, as well as a device for supplying dialysis fluid with a known inlet concentration. The device further entailing a concentration measurement sensor for measuring the concentration at the outlet of the dialyzer that is connected at least downstream of the dialyzer in the dialysate circuit. The device having an analyzer circuit connected to the output measurement signal of the concentration measurement sensor and the signal for the value of the dialysate inlet concentration and other derived measurement quantities or characteristics. The analyzer circuit generating control signals for setting the pumps in the blood or dialysis fluid circuits to a minimum of one second different pump speed. Flow measured quantities derived from the set flow value being switched to the analyzer circuit which is designed so that it determines the parameter to be determined from all applied measured quantities, taking into account the dialyzer characteristics which describe the mass exchange.

In the method according to this invention, the blood flow and the dialysate flow are varied instead of the dialysate inlet concentration. At first glance, this gives the impression that it ultimately does not matter which parameters are varied so that two unknown measured quantities can be determined with the help of two equations. However, that is not the case here: the dialysance also changes due to the change in blood flow or dialysate flow, i.e., equation systems (1) and (3) cannot be solved as easily as in the case of German Patent DE 3,938,662.

This invention offers the following advantages in comparison with the known methods and devices:

The method according to this invention also uses measured values for the inlet and outlet concentrations in the dialysate, wherein both values need not necessarily be measured; the inlet value can also be set at a defined level. However, it can also be implemented more rapidly. The inlet conductivity of the dialysis fluid need not be varied functionally. Instead, the flow rate is changed, i.e., the pump speed in terms of equipment. In contrast with the change in conductivity, this has an effect immediately at all points in the dialyzer and leads to a much shorter measurement time.

Since the changes in equilibrium in the dialyzer are not so serious, i.e., because the leaps in conductivity of the outlet dialysate are smaller, this factor also leads to a shortening of the measurement time.

Because of the shortening of the measurement time, feedback effects on the blood concentration at the inlet are also less influential. The assumption of a constant dialysance during the measurement period is eliminated. Since the dialysance depends on flow, it changes and enters directly into the determination of the parameter as a variable to be taken into account. Finally, the invention does not require any additional equipment to vary the ion concentration at the dialysate inlet of the dialyzer. All that is required in terms of equipment is a relatively simple device for adjusting the speed of the blood pump and the dialysate pump.

German Patent DE 19,541,783 C1, which was not published previously, describes a method of determining hemodynamic parameters that are factually related with the fistula flow during this extracorporeal blood treatment with a dialyzer, like the fistula flow itself, body temperature and cardiac output. To do so, a certain characteristic of the blood is measured continuously; this may be, for example, the concentration of a blood component or the hematocrit. At the same time, the blood flow is varied continuously between two limit values, and the flow values as well as the respective measured values of the characteristic are stored as a value pair. The stored sequence of value pairs permits an inference regarding the fistula flow with respect to blood flow in particular and thus an inference regarding fistula recirculation.

However, this method is not concerned with determining the parameters involved in the mass exchange of the dialyzer on the basis of measurements of the substance concentration in the dialysis fluid on the dialysate side and two discrete variables derived from two blood flow settings and/or dialysate flow settings in combination with values derived from equations between characteristics of the dialyzer describing the mass exchange in the dialyzer.

According to another embodiment of this invention, it is expedient if the blood flow (Qvb) is set at a minimum of two different values, where a signal for the effective blood flow (Qb) or for a measurement quantity linked to Qb by a known equation at least in the measurement interval is derived from the respective blood flow.

World Patent WO 95/32010, which was acknowledged in the introduction, also provides for an adjustment of blood flow, but it serves there for iterative setting of a measured value at the dialysate outlet of the dialyzer, whereas in the case of the invention, the different setting of the flow rates serves to derive measured quantities that enter directly into the determination of the value of a parameter of hemodialysis.

According to one embodiment of the invention, the dialysis fluid flow (Qd) is additionally or as an alternative set at a minimum of two different values, and a corresponding measured quantity for the dialysis fluid flow is derived in each case. This possibility yields another degree of freedom in the determination of the desired parameter of hemodialysis. In the case of German Patent DE 3,938,662 cited in the introduction, it is also provided that the dialysate flow is adjusted, but there the parameter to be determined is determined again from other measured quantities for each flow setting, i.e., a sequence of values of the parameter to be determined is derived from a sequence of the dialysate flows, whereas in the case of this invention, a single value of the parameter to be determined is derived from the different values of the dialysate flows.

Those skilled in the art have access to a number of possibilities for deriving the measured quantities for blood flow and dialysate flow, for example, directly via the output signal of a flow measurement device or indirectly via the speed setting signals for the respective pumps.

The method is preferably carried out in such a way that the inlet concentration (cdi) of the dialysate fluid is constant. This eliminates the disadvantages mentioned above due to variations in the inlet concentration of the dialysis fluid. The method according to this invention, however, makes it possible for the inlet concentration (cdi) in the dialysis fluid to vary within certain limits in the measurement interval if required by the determination of the hemodialysis parameter in the individual case.

Additional design features and embodiments of this invention are contained in the corresponding subclaims.

Figure 1:
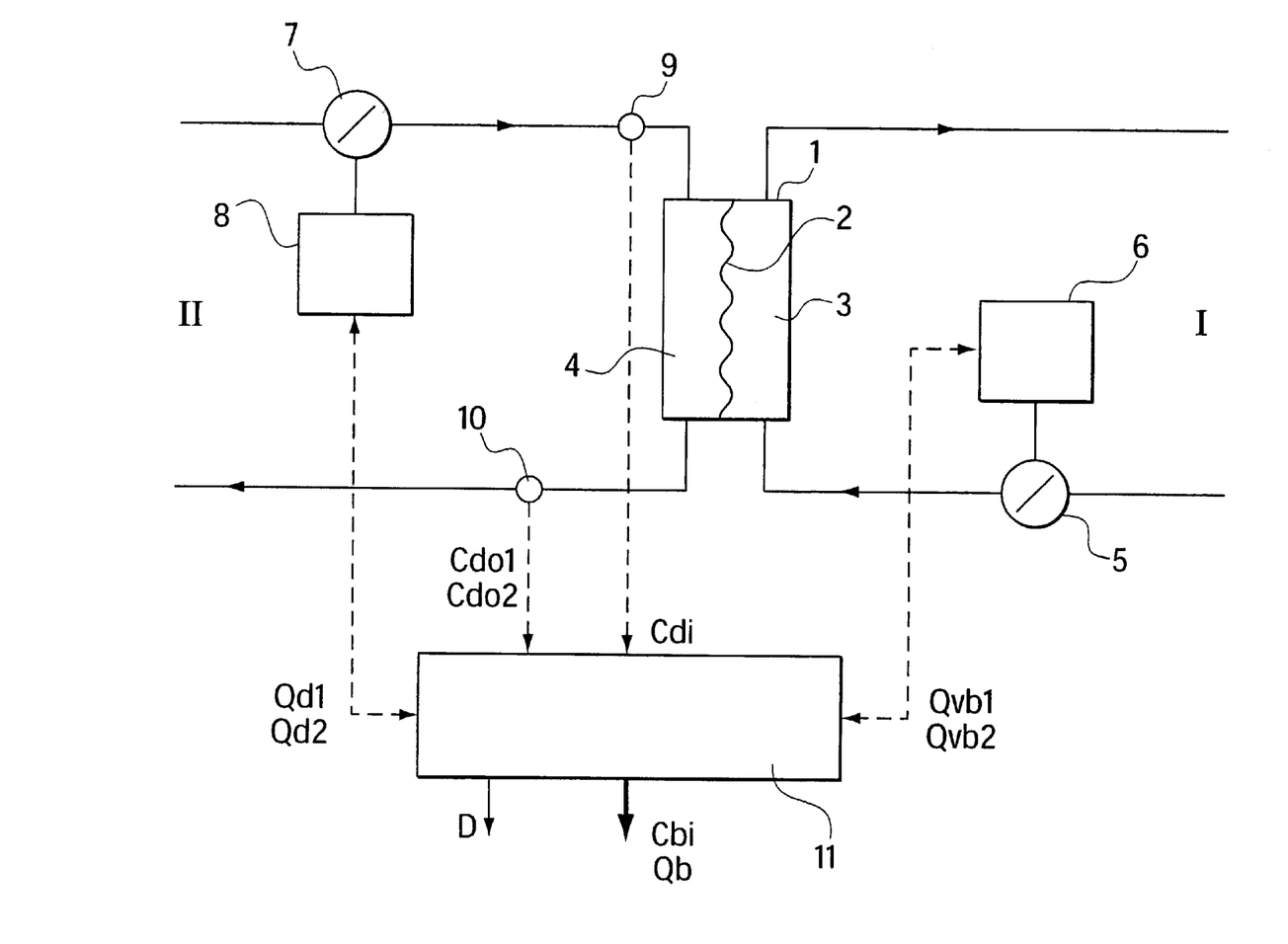
The FIGURE shows a block diagram of the device according to this invention with which the method according to this invention for in-vivo determination of hemodialysis parameters can be carried out.

This invention will now be explained in greater detail on the basis of a block diagram illustrated in the FIGURE.

DESCRIPTION OF THE PREFERRED EMBODIMENTS

The device has a dialyzer 1 with a semipermeable membrane 2 that separates a blood chamber 3 from a dialysate chamber 4. Blood chamber 3 is connected to an extracorporeal circuit I where the blood to be purified flows at a flow rate which is determined by a blood pump 5. By means of device 6, the speed of blood pump 5 and thus the whole blood flow Qvb can be changed. Such devices are state of the art, just as the remaining design of extracorporeal circuit I is likewise state of the art and therefore is not shown in the block diagram according to the FIGURE. Dialysate chamber 4 is connected to a dialysate circuit II with a conventional design, although for the sake of simplicity only a dialysate pump 7 with a respective device 8 for changing the speed of this pump and the conductivity sensors 9 and 10 are shown. A similar device is disclosed in U.S. Pat. No. 5,092,836, the disclosure of which is hereby incorporated by reference.

The conductivity sensors 9 and 10 preferably measure the temperature-corrected conductivity of the dialysis fluid on the basis of the sodium concentration. Instead of determining the conductivity, the concentration measurement can also be performed by measuring suitable optical properties.

The remaining design is known, in which regard reference is made, for example to European Patent EP 97,366 cited in the introduction. The dialysis fluid flows through dialysate chamber 4 at a flow rate Qd which is determined by the speed of pump 7 and an inlet concentration cdi which is detected by conductivity sensor 9 installed upstream. The outlet concentration cdo adjusted in dialysis is detected by the downstream conductivity sensor 10. The electrolyte transfer is calculated from the difference cdi–cdo as the basic quantity for the parameter to be determined. Alternatively, conductivity sensor 9 can be eliminated and the measured value replaced by a set value, i.e., a predetermined value, of cdi.

All signals for the flows Qb and Qd and for the concentrations cdi and cdo on the dialysate side are sent to an analyzer stage 11, preferably formed by a microprocessor which is usually present anyway in a dialysis machine. In this analyzer stage 11, the signals are linked together to determine the desired hemodialysis parameter. Thus, for example, the electrolyte transfer rate Qd×(cdi–cdo) is calculated in this stage 11, and the relationship to other variables is established on the basis of the mass balance in the dialyzer. According to this invention, at least one of the two flow rates Qb or Qd is set at a minimum of two different values via devices 6 and 8, triggered by a control signal from analyzer stage 11, where corresponding measured quantities are derived from these values and are also sent to analyzer stage 11, where they are linked to other quantities to arrive at the parameter to be determined. The linkage of these quantities is discussed below.

The whole blood flow Qvb is preferably set at two different values Qvb1 and Qvb2 by means of stage 6 and blood pump 5. However, the effective blood flow Qb is the deciding factor for dialysis. This effective blood flow is derived from the whole blood flow Qvb according to known equations (see Franz, cited above). This derivation of value Qb is also performed in analyzer stage 11.

Alternatively or additionally, the dialysis fluid flow is also set at a minimum of two different values Qd1 and Qd2, and the signals thus derived are linked with other quantities in analyzer stage 11.

The inlet concentration cdi of the dialysis fluid is preferably constant. However, the inlet concentration of the dialysis fluid can be varied within certain limits in the measurement interval in order to have another measured value.

The linkage of the measured quantities and the derived operands in the analyzer stage are explained below; first, the blood concentration at the inlet cbi at a measured effective blood flow Qb and, second, the effective blood flow at a known cbi were selected as parameters to be determined.

An equation formulation and the respective equation systems for determining the preceding parameters are presented, describing the general transition of a dialyzer from a first state to at least one other state, i.e., from a first state of a parameter with a first measurement of the value of this parameter to at least one second state with a second measurement of the parameter. The respective equations are formulated in general terms, such that certain parameters need not be kept constant between the minimum of two measurements as long as they are known or measured, or as long as certain parameter ratios are maintained. Therefore, the equation formulation and the equation systems also contain all cases in which the blood concentration at the inlet, cbi, or the inlet concentration, cdi, of the dialysis fluid, and the characteristics of the dialyzer used in the solution formulation change between the two measurements.

The equations are formulated by the mass balance according to equation (2) which is related to the characteristics that determine the mass exchange of the dialyzer.

$$Qd \cdot (cdo - cdi) = Qb \cdot (cbi - cbo) = \frac{A \cdot \overline{c}_{\ln}}{R} \quad (4, 5)$$

with the exchange area A of the dialyzer, its specific membrane diffusion resistance R, and the average concentration difference prevailing in the countercurrent process:

$$\overline{c}_{\ln} = \frac{(cbi - cdo) - (cbo - cdi)}{\ln\left(\frac{cbi - cdo}{cbo - cdi}\right)} \quad (6)$$

Equation (4) can be solved for cbo and the expression thus obtained can be inserted into (6):

$$\overline{C_{\ln}} = \frac{(cbi - cdo) - \left[cbi - \frac{Qd \cdot (cdo - cdi)}{Qb} - cdi\right]}{\ln\left[\frac{cbi - cdo}{cbi - \frac{Qd \cdot (cdo - cdi)}{Qb} - cdi}\right]} =$$

$$= \frac{cdo \cdot \left(\frac{Qd}{Qb} - 1\right) + cdi \cdot \left(1 - \frac{Qd}{Qb}\right)}{\ln\left[\frac{cbi - cdo}{cbi - cdo \cdot \frac{Qd}{Qb} + cdi \cdot \left(\frac{Qd}{Qb} - 1\right)}\right]}$$

This yields:

$$\frac{\ln\left[\frac{cbi - cdo}{cbi - cdo \cdot \frac{Qd}{Qb} + cdi \cdot \left(\frac{Qd}{Qb} - 1\right)}\right]}{\left(\frac{Qd}{Qb} - 1\right)} \cdot Qd = \frac{A}{R} \quad (7)$$

Let the equilibrium transition of the dialyzer from state Z1 (numbers with index 1) to the state Z2 (numbers with index 2) be characterized by the transition constants k1, k2, k3, where $$k1 := \frac{cbi2}{cbi1}$$

$$k2 := \frac{cdi2}{cdi1}$$

$$k3 := \frac{A2 \cdot R1}{A1 \cdot R2}$$

Thus a statement regarding the change in the three variables cbi, cdi, A/R is made in the form of $k_i$ when the system makes the transition from state Z1 to state Z2.

The characteristic A/R of the dialyzer depends on the fluid flows on the blood side and on the dialysate side, especially in high-flux dialyzers. In a certain range of flows Qd and Qb, the characteristic is constant. It is a reproducible function of Qd and Qb, i.e., the method according to this invention can also be used when there is a variation in this characteristic, if the ratio of these two characteristics in both states is known, e.g., by an in-vitro measurement, and is stored as a constant or as a function term in analyzer unit 11.

Then the following can be equated via equation (7) at the transition of the system:

$$\frac{\ln\left[\frac{cbi1 - cdo1}{cbi1 - cdo1 \cdot \frac{Qd1}{Qb1} + cdi1 \cdot \left(\frac{Qd1}{Qb1} - 1\right)}\right]}{\left(\frac{Qd1}{Qb1} - 1\right)} \cdot Qd1 \cdot k3 =$$

$$= \frac{\ln\left[\frac{k1 \cdot cbi1 - cdo2}{k1 \cdot cbi1 - cdo2 \cdot \frac{Qd2}{Qb2} + k2 \cdot cdi1 \cdot \left(\frac{Qd2}{Qb2} - 1\right)}\right]}{\left(\frac{Qd2}{Qb2} - 1\right)} \cdot Qd2$$

Condition Z1 (Qd1, Qb1, cdi1, cdo1, cbi1, A1, R1)→Condition Z2 (Qd2, Qb2, cdi2, cdo2, cbi2, A2, R2)

After an appropriate transformation of the expression with the $$q := \frac{Qd1}{Qb1}, \quad n \cdot q = \frac{Qd2}{Qb2}$$

formulation: $x \cdot \ln a = \ln a^x$, this yields with and thus $$n = \frac{Qd2 \cdot Qb1}{Qd1 \cdot Qb2}$$

$$B = \frac{Qd1 \cdot (n \cdot q - 1)}{Qd2 \cdot (q - 1)}$$

the following equation:

$$\left[\frac{k1 \cdot cbi1 - cdo2}{(k1 \cdot cbi1 - (cdo2 \cdot n \cdot q) - (k2 \cdot cdi \cdot (n \cdot q - 1)))}\right] - \quad (9)$$

$$\left[\frac{cbi1 - cdo1}{cbi1 - cdo1 \cdot q - (cdi1 \cdot (q - 1))}\right]^{k3 \cdot B} = 0$$

Equation (9) describes in general the mass exchange in the dialyzer at the equilibrium transition from state Z1 to state Z2, i.e., it establishes a connection between the two states for the variables involved. This can be analyzed in a variety of ways. If, for example, the blood concentration at the inlet cbi is to be determined, the unknown cbi is varied numerically for all values of Qd, Qb and cdi, cdo at given measured values and for given constants in equation (9) until the expression equals zero, i.e., the zero position of the respective function has been found. This mathematical measure, i.e., the numerical search for the zero position, can be performed relatively quickly in analyzer stage 11 with today's computers and appropriate programming.

It is self-evident that equation (9) is only a preferred mathematical representation. However, the invention covers all equivalent expressions, i.e., all mathematical conversions or approximations of equation (9).

As a result of the above solving of equation (9), the value of the blood concentration at the inlet cbi is obtained. Starting with this value, additional hemodialysis parameters, e.g., the dialysance or clearance, can then be determined. To determine the two values for the dialysance at the two flows, equation (3) or an adequate equation for Qb is used. This computation process is also used in microprocessor 11.

The various parameters and characteristics contained in equation (9) and some advantageous settings for solving the equation are listed below:

k1 known, advantageously=1 (cbi is constant or is varied in a known way), k2 is known, advantageously=1 (cdi is constant or is varied in a known way), k3 is known, advantageously=1 (A/R is constant or is varied in a known way), Qd1, Qd2 both known, especially advantageously with Qd1=Qd2, Qb1, Qb2 known, cdo1, cdo2 known.

In solving equation (9) for cbi, two blood flow settings are assumed, the first blood flow Qb1 which is given and the second blood flow Qb2 which is advantageously lower. In general, the absolute whole blood flow Qvb is measured. This measurement is known to be subject to errors. First, as mentioned above, the hematocrit, which must be determined with it additionally, enters into the determination of the effective blood flow Qb from this measured value. Second, hematocrit varies over the hemolysis time as a result of the ultrafiltration.

In addition, it should also be pointed out that the whole blood flow is only approximately known because it is usually determined on the basis of the hose diameter of the system and the rotational speed of the peristaltic blood pump which is generally used. Since the hose diameter is typically known only with an accuracy of +/−5%, and furthermore since the pump segment cross section can be reduced by the intake vacuum, this also yields a considerable tolerance.

According to one embodiment of this invention, the effective blood flow Qb can be determined from equation (9) as the desired parameter or as an interim value if the value cbi, the blood concentration at the inlet, is known according to any method, preferably by the bypass method according to Patent Application 197 34 992.7. Equation (9) is then solved for Qb.

Thus, the method according to this invention not only offers the possibility of measuring the blood concentration at the inlet cbi and the in-vivo dialysance or clearance, but also makes it possible to measure the absolute blood water content or the amount of cellular components, or the hematocrit (HCT) can be measured in the blood because the effective blood flows Qb1, Qb2 determined with equation (9) with a known cbi can be compared with the pump volume Qvb delivered by the blood pump, which contains not only the aqueous component but also the solid constituents. For the simplified case where the plasma water is the only solvent for the respective substance, the following equations hold:

$$HCT = 1 - \frac{Qb1}{Qvb1} = 1 - \frac{Qb2}{Qvb2} = 1 - \frac{Qb3}{Qvb3}$$

This yields various possibilities for the field of physiological dialysis. Thus, for example, it is possible to determine a change in the patient's blood volume. Such a change in blood volume is known to lead to a change in hematocrit and the aqueous component of blood.

The prerequisite, however, is that the transport properties of the dialysis membrane remain unchanged, i.e., there is no partial blockade of the membrane. However, such disturbances in hemodialysis can be detected by suitable detectors.

In addition, changes in transport properties of the membrane can be deduced by means of this method, if other methods of determining the change in blood volume are available. Thus, changes in the transport property of the membrane can be determined from a comparison of the changes in clearance thus calculated with the measured change.

Additional examples of applications are conceivable.

The invention is not limited to the embodiments and possible applications presented here; instead, there are various refinements within the scope of this invention, in particular with regard to the variation in the respective parameters. Thus, this invention can be applied in extension of the term "dialyzer with membrane" in general with an exchange apparatus having a semipermeable separation layer. Blood need not necessarily be one of the two fluids; in principle, the method according to this invention can be applied to the metabolism between any two fluids. Furthermore, exchange processes in a heat exchanger can also be quantified in this way.

What is claimed is:

1. A method for the in vivo determination of a hemodialysis parameter involving a dialyzer having a semipermeable separation layer between a blood chamber and a dialysate chamber, comprising the steps of providing blood to the blood chamber and dialysate to the dialysate chamber, varying the dialysance by varying the flow rate of at least one of the blood flow and dialysate flow, the blood flow and the dialysate flow, respectively being varied over at least two respective predetermined flow rates during a measuring interval, obtaining the concentration of a substance in the dialysate upstream and downstream of the dialysate chamber at the predetermined flow rates, and determining a hemodialysis parameter from the obtained concentrations of the substance and the at least two predetermined flow rates using relationships between the characteristic quantities of the dialyzer describing the substance exchange.

2. The method of claim 1, further comprising setting the blood flow rate to at least two different predetermined values, and deriving a signal for the effective blood flow from the prevailing blood flow.

3. The method of claim 1, further comprising setting the blood flow rate to at least two different predetermined values, and deriving a signal from the prevailing blood flow rate for a measured quantity linked to the effective blood flow at least in the measuring interval by way of a known equation.

4. The method of claim 1, further comprising setting the dialysate flow rate to at least two different predetermined values, and measuring the substance concentration at each dialysate flow rate.

5. The method of claim 1, further comprising maintaining a constant dialysate inlet concentration.

6. The method of claim 1, further comprising varying the dialysate inlet concentration within a predetermined range during the measuring interval.

7. The method of claim 1, wherein the effective blood flow is measured, and the blood inlet concentration is determined.

8. The method of claim 1, wherein the blood inlet concentration is measured, and the effective blood flow is determined.

9. The method of claim 7, further comprising determining the dialysance or the clearance of the dialyzer from the blood inlet concentration.

10. A method for the in vivo determination of a hemodialysis parameter involving a dialyzer having a semipermeable separation layer between a blood chamber and a dialysate chamber, comprising the steps of;

providing blood to the blood chamber and dialysate to the dialysate chamber;

varying the dialysance by varying the flow rate of at least one of the blood flow and dialysate flow, the blood flow and the dialysate flow being respectively varied over at least two respective predetermined flow rates during a measuring interval;

obtaining the concentration of a substance in the dialysate upstream and downstream of the dialysate chamber at the predetermined flow rates; and determining the hemodialysis parameter from the measured quantities cd, cb, Qd, Qb, the exchange surface A of the dialyzer, and the specific membrane diffusion resistance R, according to the equation:

$$\left[\frac{k1 \cdot cbi1 - cdo2}{(k1 \cdot cbi1 - (cdo2 \cdot n \cdot q) - (k2 \cdot cdi \cdot (n \cdot q - 1)))}\right] -$$

$$\left[\frac{cbi1 - cdo1}{cbi1 - cdo1 \cdot q - (cdi1 \cdot (q-1))}\right]^{k3 \cdot B} = 0$$

with $$n = \frac{Qd2 \cdot Qb1}{Qd1 \cdot Qb2}$$

$$q := \frac{Qd1}{Qb1}, \quad n \cdot q = \frac{Qd2}{Qb2}$$

$$B = \frac{Qd1 \cdot (n \cdot q - 1)}{Qd2 \cdot (q - 1)}$$

and the transition constants $$k1 := \frac{cbi2}{cbi1}$$

$$k2 := \frac{cdi2}{cdi1}$$

$$k3 := \frac{A2 \cdot R1}{A1 \cdot R2}$$

wherein cd is a concentration in the dialysate; cb is a concentration in the blood; Qd, is a dialysate flow and Qb is an effective blood flow.

11. A method for the in vivo determination of a hemodialysis parameter involving a dialyzer having a semipermeable separation layer between a blood chamber and a dialysate chamber, comprising;

providing blood to the blood chamber and dialysate to the dialysate chamber;

varying the dialysance by varying the flow rate of at least one of the blood flow and dialysate flow, the blood flow and the dialysate flow being respectively varied over at least two respective predetermined flow rates during a measuring interval;

obtaining the concentration of a substance in the dialysate upstream and downstream of the dialysate chamber at the predetermined flow rates;

determining a hemodialysis parameter from the obtained concentrations of the substance and the at least two predetermined flow rates using relationships between the characteristic quantities of the dialyzer describing the substance exchange;

measuring the blood inlet concentration and determining the effective blood flow, and determining the hematocrit from the effective blood flow and a measured value for the whole blood flow, according to the formula:

$$HCT = 1 - \frac{Qb}{Qvb}$$

wherein Qb is an effective blood flow and Qvb is a blood flow.

12. A device for the in vivo determination of hemodialysis parameters comprising a dialyzer having a semipermeable separation layer separating a blood chamber from a dialysate chamber, the blood chamber adapted for connection to a patient by a blood circulation system having a blood pump, the dialysate chamber adapted for connection to a dialysate circulation system having a dialysate pump, at least one of the blood circulation system and the dialysate circulation system having a device for varying the dialysance of the dialyzer by varying the respective fluid flow rate, the respective fluid flow rate being variable over at least two rates, a sensor adapted to measure the concentration of dialysate at the outlet of the dialysate chamber, means connected to the sensor for setting at least one of the blood and dialysate flow rates to at least two predetermined flow rates, and means for determining a hemodialysis parameter from the measured substance concentrations at the at least two predetermined flow rates, and using relationships between the characteristic quantities of the dialyzer describing the substance exchange.

13. The device of claim 12, wherein the sensor is selected from the group consisting of a conductivity sensor and an optical sensor.

* * * * *

UNITED STATES PATENT AND TRADEMARK OFFICE
CERTIFICATE OF CORRECTION

PATENT NO. : 6,217,539 B1
DATED : April 17, 2001
INVENTOR(S) : Rainer Goldau

It is certified that error appears in the above-identified patent and that said Letters Patent is hereby corrected as shown below:

Column 1,
Line 46, delete "iS".

Signed and Sealed this

Eighth Day of January, 2002

Attest:

JAMES E. ROGAN
Attesting Officer  Director of the United States Patent and Trademark Office